United States Patent [19]
Goltra

[11] Patent Number: 5,812,984
[45] Date of Patent: Sep. 22, 1998

[54] METHOD FOR ENTERING INFORMATION INTO AN ELECTRONIC PATIENT CHART, AND PROTOCOL AUTO-NEGATIVE CAPABILITIES

[76] Inventor: Peter S. Goltra, 22717 Goltra La., Middleburg, Va. 22117

[21] Appl. No.: 645,119

[22] Filed: May 13, 1996

[51] Int. Cl.⁶ .......................... G06F 17/30; G06F 15/20
[52] U.S. Cl. ........................ 705/3; 600/300; 707/104
[58] Field of Search .......................... 705/2, 3; 600/300, 600/301

[56] References Cited

U.S. PATENT DOCUMENTS

| | | | |
|---|---|---|---|
| 4,130,881 | 12/1978 | Haessler | 364/900 |
| 4,839,822 | 6/1989 | Dormond et al. | 306/45 |
| 4,878,175 | 10/1989 | Norden-Paul et al. | 364/413.01 |
| 5,077,666 | 12/1991 | Brimm et al. | 364/413.02 |
| 5,089,978 | 2/1992 | Lipner et al. | 702/183 |
| 5,107,419 | 4/1992 | MacPhail | 395/600 |
| 5,262,943 | 11/1993 | Thibado et al. | 600/300 |
| 5,265,010 | 11/1993 | Evans-Paganelli et al. | 364/413.02 |
| 5,387,164 | 2/1995 | Brown, Jr. | 482/9 |
| 5,623,925 | 4/1997 | Swenson et al. | 128/630 |
| 5,664,270 | 9/1997 | Bell et al. | 5/600 |
| 5,682,526 | 10/1997 | Smokoff et al. | 395/615 |
| 5,704,371 | 1/1998 | Shepard | 128/897 |

*Primary Examiner*—Kevin J. Teska
*Assistant Examiner*—Hani M. Kazimi
*Attorney, Agent, or Firm*—Burns, Doane, Swecker & Mathis, L.L.P.

[57] ABSTRACT

A method for entering information into an electronic patient chart is disclosed. The electronic patient chart is comprised of at least one protocol wherein each protocol may be divided into a plurality of sections each of which containing a plurality of medical findings. First, a user is prompted with a plurality of medical findings within at least a section of a protocol or a template. The user then enters positive responses for various, if any, medical findings based upon a patient's answers or conditions. Once the positive responses have been entered into this section of the protocol, the system on command or in the alternative when the section of the protocol is exited automatically marks all or selected types of the remaining unmarked medical findings with negative responses.

14 Claims, 3 Drawing Sheets

METHOD FOR ENTERING INFORMATION INTO AN ELECTRONIC PATIENT CHART, AND PROTOCOL AUTO-NEGATIVE CAPABILITIES

FIELD OF THE INVENTION

The present invention relates to a method for creating patient charts by healthcare professionals, and more particularly to a method for automatically entering information into a protocol within a patient chart.

BACKGROUND OF THE INVENTION

While many aspects of the operation and administration at hospitals and other healthcare facilities have been computerized over the past years, one of the most important aspects, the generation of patient charts, the updating of these charts, the review of the chart, and the generation of care plans by healthcare professionals such as doctors, nurses, therapists, and the like, is still performed largely by hand. As a result, while a patient chart of some type is normally generated shortly after a patient is admitted to the healthcare facility for a particular service, for example, an intensive care unit, cardiac surgery unit, or the like, the chart may not always be updated to reflect actual progress by the patient.

When a patient comes into a health care facility, the patient may have numerous related or unrelated problems that the healthcare provider will have to sort through when determining what is wrong with the patient and what treatments should be prescribed for the patient. Manually reviewing the chart for previous clinical findings relevant to the current problems can be a very time consuming and error-prone procedure. The diagnostic step in the treatment of the patient can thus be a very difficult process and arguably the most important step in treating a patient. Today, most healthcare professionals must rely on their memory and experience as well as written materials when making a diagnosis. Unfortunately, all of the needed materials may not be available during the examination of the patient and thus important questions may not be asked or tests performed which could help the healthcare professional in determining the correct diagnosis for the problems being experienced by the patient. Thus, it would be advantageous to allow healthcare professionals to create medical protocols which prompt the healthcare professional with lists of questions that should be asked, physical findings to look for, and tests that should be run, during the encounter.

Presently, computer based patient chart and/or progress note systems are available to help healthcare professionals with the patient care. However, such systems lack the flexibility so as to be configurable by the healthcare professionals so as to provide specific help in determining diagnoses and for prompting the healthcare professional with lists of symptoms, questions which should be asked and tests that should be performed in certain circumstances. Another problem which can occur when using computer based patient charts is that patients may perceive the encounter with the healthcare professional as being impersonal if the healthcare professional is always staring at a computer screen. Furthermore, patients may become nervous or uncomfortable if a healthcare professional has to enter too much information into the computer based patient chart. Thus, there is a need for minimizing the amount of time a healthcare professional spends entering the relevant information into a computer based patient chart.

SUMMARY OF THE INVENTION

In a patient encounter a physician/healthcare professional will typically ask the patient a series of questions. Next, the healthcare professional will examine the patient, make an assessment of any problems which may be present, and perhaps order a series of tests to confirm the diagnosis. If a computer-based chart is to be used, a mechanism to facilitate the entry of the information is important. It is an object of the present invention to provide such a mechanism which is easy to use.

According to one embodiment of the invention, a method for entering information into an electronic patient chart is disclosed. The electronic patient chart is comprised of at least one protocol wherein each protocol may be divided into a plurality of sections each of which containing a plurality of medical findings. First, a user is prompted with a plurality of medical findings within a section of a protocol. The user then enters positive responses for various, if any, medical findings based upon a patient's answers or conditions. Once the positive responses have been entered into this section of the protocol, the system on command or in the alternative when the section of the protocol is exited automatically marks all or selected types of the remaining unmarked medical findings with negative responses.

According to another embodiment of the invention, a method for entering information into an electronic patient chart is disclosed. The electronic patient chart is comprised of at least one protocol each of which contain a plurality of medical findings. First, a user is prompted with the medical findings within one of the protocols. The user then enters positive responses for various, if any, medical findings based upon the patient's answers or conditions discovered during an examination. Once the positive responses have been entered into the protocol, the system either on command or in the alternative when the protocol is exited automatically marks all or selected types of the remaining unmarked medical findings in the protocol with negative responses.

BRIEF DESCRIPTION OF THE DRAWING FIGURES

These and other features and advantages of the invention will be readily apparent to one of ordinary skill in the art from the following written description, used in conjunction with the drawings, in which.

DESCRIPTION OF THE PREFERRED EMBODIMENTS

Figure 1:
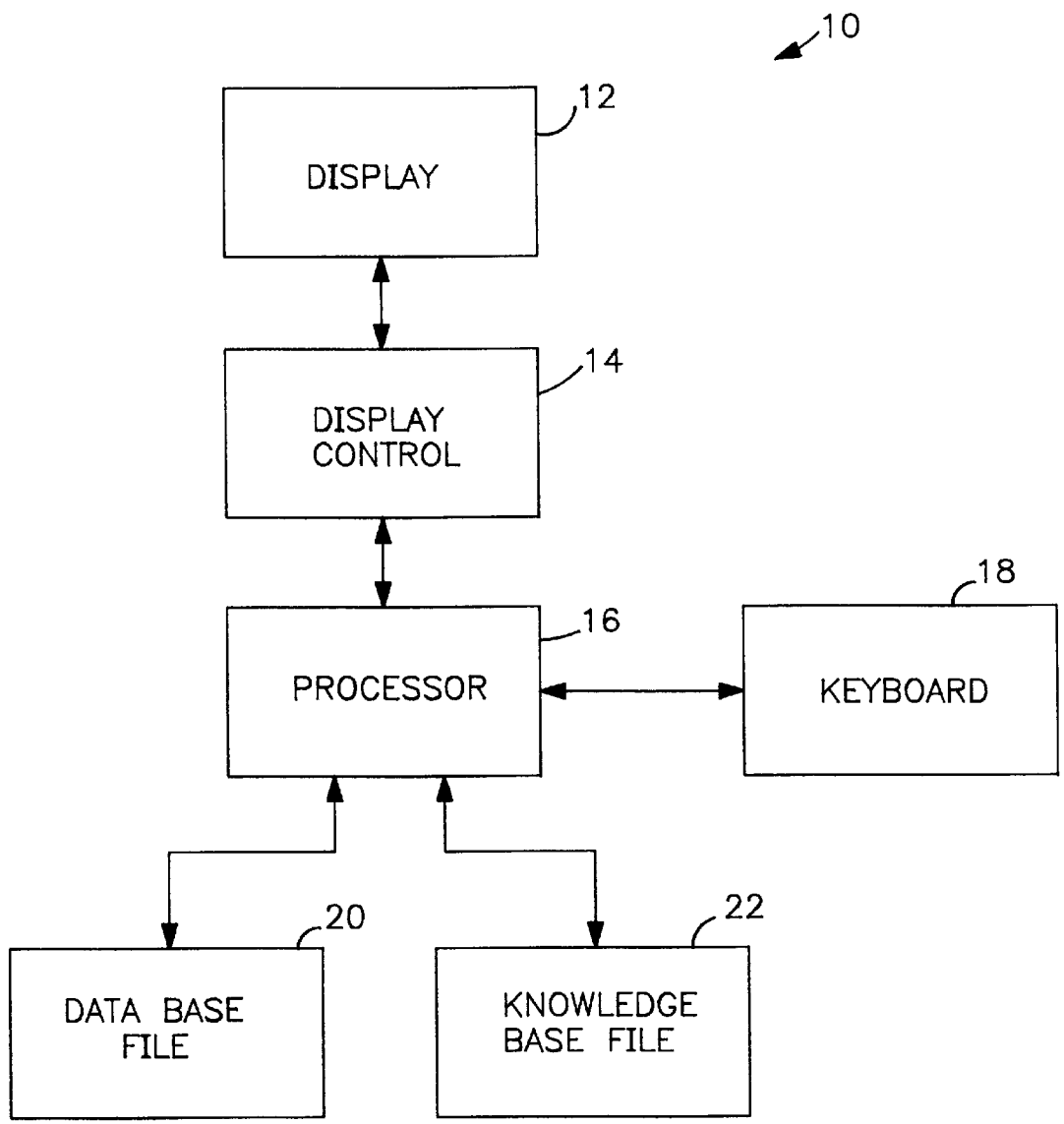
FIG. 1 illustrates a block diagram of a computer-based medical system according to one embodiment of the present invention.

The present invention uses a computer based medical system to allow a healthcare professional to chart the progress of a particular patient. A block diagram of the computer based medical system suitable for use in practicing the teachings of the present invention is illustrated in FIG. 1. The medical system 10 contains a processor 16 with one or more input devices such as a keyboard 18. The processor 16 also has a database file or memory 20 and a knowledge base file or memory 22. The processor 16 operates a standard display controller 14 which in turn, controls a display device 12 at the work station. The display device 12 can be any standard type of display monitor, attached or wireless. Furthermore, the apparatus 10 can be networked to other such medical systems not illustrated which can be placed around a hospital or healthcare facility. This allows multiple people to use the medical system for the same or for multiple patients.

The present invention is based upon on medical findings. Medical findings are defined as symptoms, history, physical findings, diagnoses, tests, and therapy which may be present for a particular patient. The database file 20 contains over 50,000 such medical findings and are divided into categories such as symptoms, history, physical findings, diagnoses, tests, and therapy. Furthermore, the descriptions of the medical findings stored in the database file 20 are hierarchical and can have up to eight levels of description. The first level gives the simplest explanation of a medical finding, for example, a cough. The explanations become more detailed the lower the level. As noted above, a first level finding may be a cough, while a second level finding may be a brassy cough. Another feature of the database memory 20 is that all of the medical findings are coded so as to be distinct from each other. For example, each medical finding can be assigned an internal number which uniquely identifies that particular medical finding. In addition, each medical finding also contains a code which indicates which category within the database file 20 the medical finding is associated with. For example, a medical finding may contain the code SYM to indicate that the medical finding is associated with the symptom section; HIS to indicate that the medical finding is associated with the history section; PHY to indicate that the medical finding is associated with the physical section; DIS to indicate that the medical finding is associated with the diagnoses section; TST to indicate that the medical finding is associated with the test section; and RX to indicate that the medical finding is associated with the therapy section.

As noted above, the medical system 10 also contains a knowledge base file 22. The knowledge base file contains a detailed description of over 2,000 diagnoses. The detailed description of the diagnoses uses the medical finding terms which are stored in the database file 20. For each diagnosis, each medical finding associated with the diagnosis is assigned a numerical value depending on how important such a medical finding may be to the diagnosis. For example, in the detailed description of the diagnosis for coronary artery stenosis, medical findings such as chest pain or discomfort and dyspnea (shortness of breath), which are strong showings of coronary artery stenosis, will be given high values while a lack of a desire for food may not be described in the diagnoses at all or given a very low value. In one embodiment of the present invention, medical findings are assigned values between 1 and 20 wherein the value 20 indicates the most important medical finding, however the invention is not limited thereto. Thus, the values assigned to each medical finding within the detailed description is proportional to how important such a medical finding is to the diagnosis. Furthermore, the values can vary for a given medical finding depending on a plurality of factors such as age of the patient and timeframe, i.e., when a symptom occurred in relation to other symptoms. For example, a white blood cell count of 18,000 may be given a high value if the patient is an adult while the same medical finding is not given a value at all if the patient is a new-born child because this is normal for a new-born child.

Here again, the medical findings used in the detailed descriptions of the diagnoses are all coded. In addition, over 400,000 links are provided between the database file 20 and the knowledge base file 22. In other words, the findings in the database file 20 occur over 400,000 times in the knowledge base file 22.

The detailed description of the diagnoses stored in the knowledge base file 22 contains lists of symptoms which a patient should or may have experienced as well as personal and family history. In addition, the detailed diagnoses contain lists of physical findings, tests, possible therapies, and medications which should be prescribed for the patient if the healthcare professional decides that the patient is experiencing a particular illness or problem.

A method and apparatus for creating and using reusable medical protocols to create patient charts is disclosed in U.S. patent application Ser. No. 08/609,828, entitled "Creating and using Protocols To Create and Review a Patient Chart", which is incorporated herein by reference. The clinical protocols are a structured combination of coded medical phrases selected from a structured medical database of coded phrases and are presented in the order of appearance selected by the healthcare professional. The healthcare professional can create a patient chart by selecting the desired phrases from the clinical protocol reflecting the responses from the patient to his/her questions or results from his/her examination, assessment, or other pertinent information the healthcare professional wishes to enter. Since the phrases are coded, upon selection of the phrases from the clinical protocol, the entered information is automatically structured in the chart in the same format as the format used in the medical database used to build the protocols. That is, symptoms automatically go into the symptoms section, physical findings into the physical examination section, diagnosis into the assessment section, etc. Since the healthcare professional who builds the clinical protocols can put in any combination of coded medical finding phrases, the protocols have a wide variety of uses. They can be used for routine examinations. They can also be used for a specific problem, such as the flu or angina. They can also be used for specific situations where a specified set of questions must always be asked or where certain information needs to be passed along to the patient. By using the protocol, nothing will be forgotten, since all the questions and the information are prompted each time the protocol is used.

The clinical protocols can be stored and used again when the patient returns either for entry of new visit information or equally important, as a mechanism to review the chart. In the latter use, the patient's chart is matched against the protocol. Since all the findings are coded, a healthcare professional can quickly see which findings in the chart are present that match the medical findings in the protocol. For example, after several visits to the healthcare professional for various problems, the patient's chart may contain hundreds or thousands of medical findings. When the patient returns complaining of a previous problem, the healthcare professional can select the matching option so as to compare the findings in a protocol for the possible problem with the medical findings in the patients chart.

Furthermore, clinical protocols and other findings can be merged together into a useful structure, i.e., a template, for a particular patient. Since the protocols are created from a structured medical database of coded phrases, it is possible to merge them together with the resulting combination retaining the medical structure of the database. In other words, the template will be divided into the same sections of medical findings that occur in the protocols. The creation of templates is described in U.S. patent application Ser. No. 08/609,523, entitled "Creation of Templates From Protocols and Other Sources", and is incorporated herein by reference.

When a healthcare professional is taking a history of a patient or is determining physical findings during the physical examination of a patient, the healthcare professional can use specially designed protocols or templates. When using the protocols or templates, the healthcare professional is prompted with a list of medical findings. The medical findings may be, for example, a list of questions which should be asked regarding the patient's condition, a list of possible symptoms, etc.. For example, a history protocol may consist of twenty medical findings. The healthcare professional will then have to ask the patient about the twenty items in the protocol. Usually, the doctors will know most of the questions by heart, and thus can ask all the questions without referring to the computer screen. This is important because healthcare professionals wish to have minimal breaks in eye contact with their patients.

Figure 2:
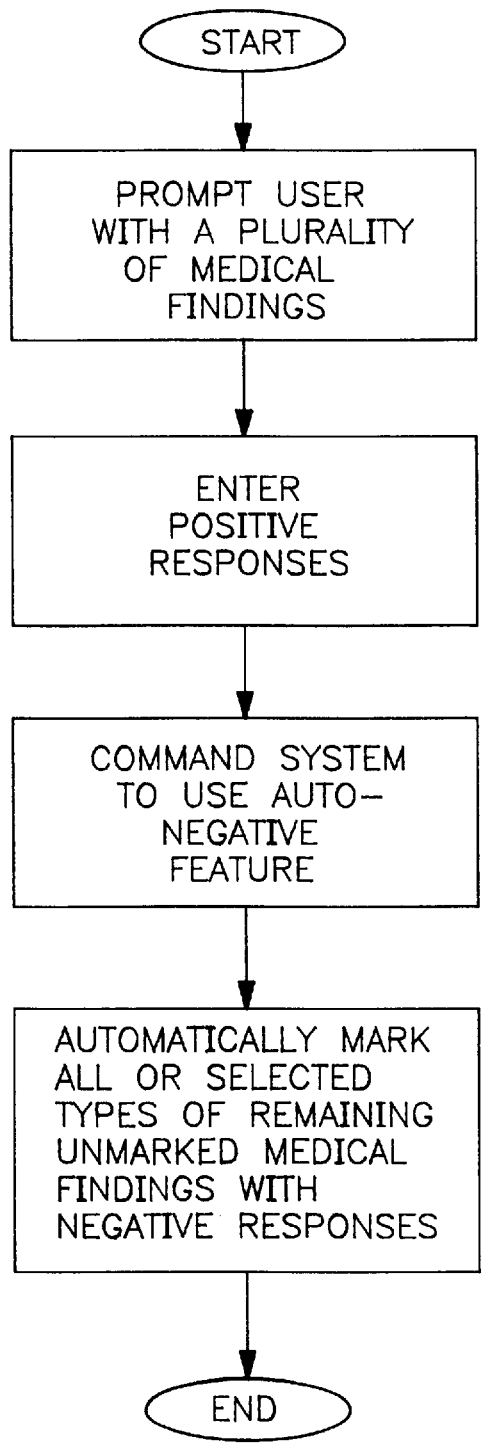
FIG. 2 illustrates a flowchart according to the operation of one embodiment of the present invention.
Figure 3:
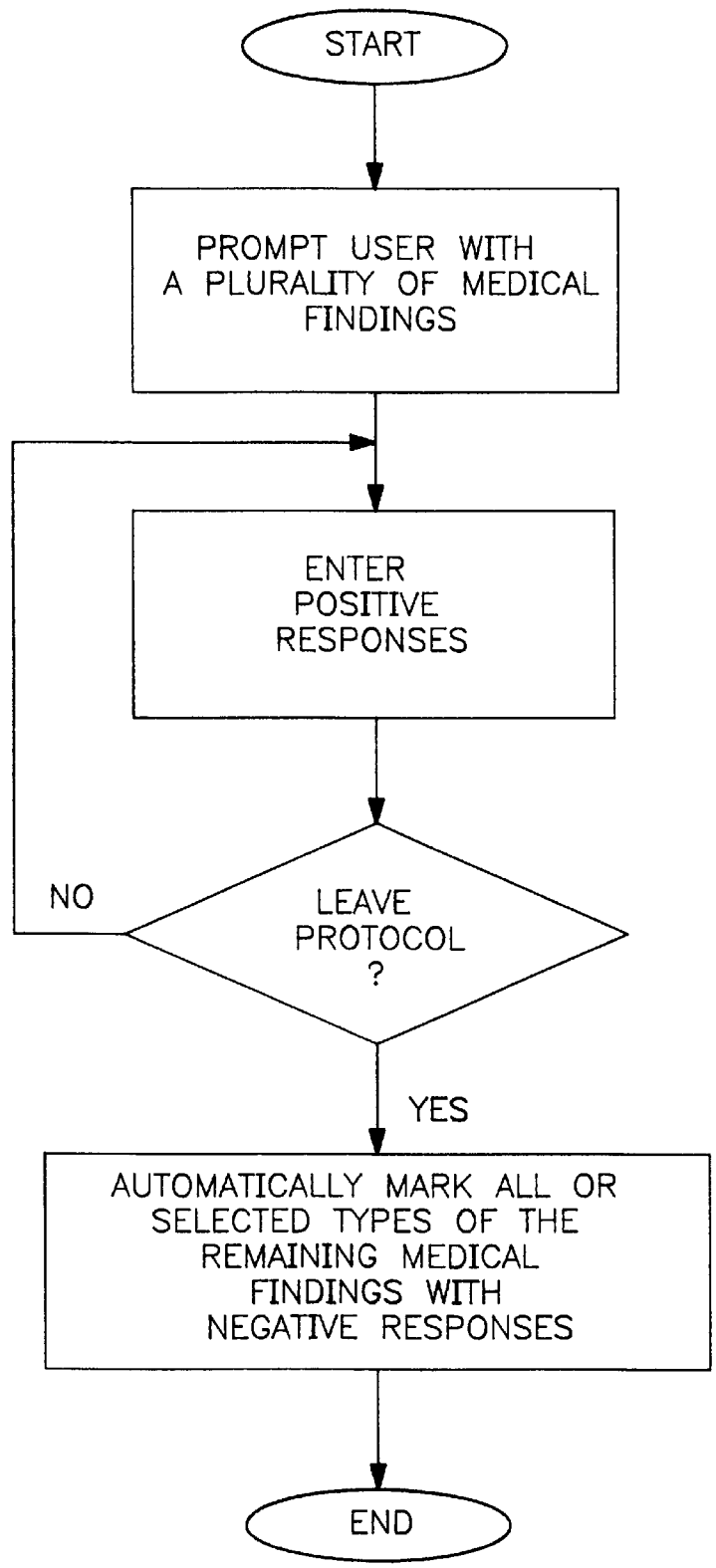
FIG. 3 illustrates a flowchart according to the operation of another embodiment of the present invention.

When the healthcare professional asks the patient about the medical findings in the protocol, the healthcare professional will have to enter positive and negative responses to the findings indicating whether they are present for the patient's condition. This can be a time consuming process and also requires the healthcare professional to be staring at the computer screen rather than at the patient. Thus, according to the present invention as illustrated in FIG. 2, the electronic patient chart can be equipped with an auto-negative capability. In other words, the healthcare professional only enters responses for positive medical findings. Then, the system on command from the healthcare professional or automatically will mark all or selected types of the remaining unmarked medical findings in the protocol, section of the protocol, or template with a negative response. It will be understood that the system can either prompt the healthcare professional asking whether the auto-negative feature should be selected or the healthcare professional can select the auto-negative feature from a list of options. In another embodiment of the present invention, the system will automatically mark all or selected types of the remaining unmarked medical findings in the protocol, section of the protocol, or template with negative responses when the healthcare professional decides to leave the protocol, section of the protocol, or template unless this feature has been previously disabled, as illustrated in FIG. 3.

Thus, if a history protocol contains twenty medical findings and only five of the medical findings are present, i.e., positive, the healthcare professional need only enter the five positive responses and the system will enter the remaining fifteen negative responses automatically. It will be understood that the system can also be configured to have an auto-positive capability as well, wherein the healthcare professional enters negative responses and the system then on command or when the protocol, section of the protocol, or template is exited automatically marks the other responses with a positive indication.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A method for entering information into an electronic patient chart made up of at least one protocol, wherein a protocol comprises a plurality of medical findings, comprising the steps of:

prompting a user with a plurality of medical findings, wherein each finding is assigned at least one numerical value that indicates an importance of the finding to each diagnosis;

entering positive responses into at least a first section of a protocol for possibly some of said medical findings;

automatically marking upon command from said user all or selected types of remaining unmarked findings within said at least first section of said protocol with a negative response.

2. A method according to claim 1, wherein said at least first section of said protocol includes patient history.

3. A method according to claim 1, wherein said at least first section of said protocol includes physical findings.

4. A method for entering information into an electronic patient chart made up of at least one protocol, wherein a protocol comprises a plurality of medical findings, comprising the steps of:

prompting a user with a plurality of medical findings, wherein each finding is assigned at least one numerical value that indicates an importance of the finding to each diagnosis;

entering positive responses into a template, said template comprising at least one protocol and medical findings, for possibly some of said medical findings;

automatically marking upon command from said user all or selected types of remaining unmarked findings within said template with a negative response.

5. A method for entering information into an electronic patient chart made up of at least one protocol, wherein a protocol comprises a plurality of medical findings, comprising the steps of:

prompting a user with a plurality of medical findings;

entering positive responses into a first section of a protocol for possibly some of said medical findings;

exiting said first section of said protocol; and automatically marking all or selected types of remaining unmarked medical findings within said at least first section of said protocol with negative responses when said at least first section of said protocol is exited.

6. A method according to claim 5, wherein said automatic marking of the remaining medical findings with negative responses can be disabled before exiting said first protocol.

7. A method according to claim 5, wherein said at least first section of said protocol includes patient history.

8. A method according to claim 5, wherein said at least first section of said protocol include physical findings.

9. A method for entering information into an electronic patient chart made up of at least one protocol, wherein a protocol comprises a plurality of medical findings, comprising the steps of:

prompting a user with a plurality of medical findings;

entering positive responses into a template, said template comprising at least one protocol and medical findings, for possibly some of said medical findings;

exiting said protocol; and automatically marking all or selected types of remaining unmarked medical findings with negative responses when said protocol is exited.

10. A method according to claim 9, wherein said automatic marking of the remaining medical findings with negative responses can be disabled before exiting said protocol.

11. A method for entering information into an electronic patient chart made up of at least one protocol, wherein a protocol comprises a plurality of medical findings, comprising the steps of:

prompting a user with a plurality of medical findings, wherein each finding is assigned at least one numerical value that indicates an importance of the finding to each diagnosis;

entering negative responses into at least a first section of a protocol for possibly some of said medical findings;

automatically marking upon command from said user all or selected types of remaining unmarked medical findings with positive responses.

12. A method according to claim 11, wherein said at least first section of said protocol includes patient history.

13. A method according to claim 11, wherein said at least first section of said protocol includes physical findings.

14. A method for entering information into an electronic patient chart made up of at least one protocol, wherein a protocol comprises a plurality of medical findings, comprising the steps of:

prompting a user with a plurality of medical findings, wherein each finding is assigned at least one numerical value that indicates an importance of the finding to each diagnosis;

entering negative responses into a template, said template comprising at least one protocol and medical findings, for possibly some of said medical findings;

automatically marking upon command from said user all or selected types of remaining unmarked findings within said template with a positive response.

* * * * *